United States Patent
Laborde et al.

(10) Patent No.: US 6,251,689 B1
(45) Date of Patent: Jun. 26, 2001

(54) METHODS FOR THE SOLID PHASE SYNTHESIS OF COMBINATORIAL LIBRARIES OF BENZIMIDAZOLES BENZOXAZOLES BENZOTHIAZOLES AND DERIVATIVES THEREOF

(75) Inventors: Edgardo Laborde; Yukiharu Matsumoto, both of Foster City, CA (US)

(73) Assignee: TELIK, Inc., San Francisco, CA (US)

( * ) Notice: Subject to any disclaimer, the term of this patent is extended or adjusted under 35 U.S.C. 154(b) by 0 days.

(21) Appl. No.: 09/313,568

(22) Filed: May 14, 1999

Related U.S. Application Data (60) Provisional application No. 60/085,465, filed on May 14, 1998.

(51) Int. Cl.[7] .................................................. G01N 33/543
(52) U.S. Cl. ..................... 436/518; 548/180; 548/222; 548/224; 548/307.4; 548/310.7; 525/383; 436/7.1; 436/518; 436/536; 436/DIG. 22; 436/DIG. 34; 436/DIG. 40; 436/DIG. 42; 436/DIG. 46; 436/DIG. 48; 436/DIG. 49
(58) Field of Search ................................ 548/126, 180, 548/222, 224, 307.4, 310.7; 436/7.1, 518, 536, DIG. 22, DIG. 34, DIG. 40, DIG. 42, DIG. 46, DIG. 48, DIG. 49; 525/383

(56) References Cited

U.S. PATENT DOCUMENTS

| | | |
|---|---|---|
| 4,258,198 | 3/1981 | Gyurik et al. . |
| 5,840,500 | 11/1998 | Pei et al. . |
| 5,847,150 | 12/1998 | Dorwald . |
| 5,852,028 | 12/1998 | Suto et al. . |
| 5,856,107 | 1/1999 | Ostresh et al. . |
| 5,856,496 | 1/1999 | Fagnola et al. . |
| 5,859,027 | 1/1999 | Kruse et al. . |
| 5,861,532 | 1/1999 | Brown et al. . |

OTHER PUBLICATIONS

Sun et al., "Single Bead IR Monitoring of a Novel Benzimidazole Synthesis," Bioorg. Med. Chem. Lett., 8: 361–4, 1998.*

Lown et al., "Convenient Routes to Substituted Benzimidazoles and Imidazolo[4,5–b]Pyridines Using Nitrobenzene as Oxidant," Synthetic Comm., 20(7), 955–963, 1990.*

Gordon et al., "Applications of Combinatorial Technologies to Drug Discovery. 2. Combinatorial Organic Synthesis, Library Screening Strategies and Future Directions," J. Med. Chem., vol. 37, No. 10, 1385–1401, 1994.*

Sharma et al., "2–Aminobenzimidazoles in Organic Synthesis," Synthesis, 861–882, 1983.*

Katsura et al., "Studies On Antiulcer Drugs. II. Synthesis and Antiulcer Activities of Imidazo [1,2–a] Pyridinyl–2–Alkylaminobenzoxazoles and 5,6,7,8–Tetrahydroimidazo[1,2–a]Pyridinyl Derivatives", Chem. Pharm. Bull., 40(2): 371–80, 1992.

Ben–Alloum et al., "Nouvelle Voie de Synthese des 2–Arylbenzothiazoles Transfert d'Electrons Active par Micro–ondes," Tetrahedron Lett., vol. 38, No. 36, 6395–6396, 1997.

Balkenhohl, F., et al, "Combinatorial Synthesis Of Small Organic Molecules," Angew. Chem. Int. Ed. Engl., (1996) 35:2288–337.

Cereda, E., et al., "Anti–Secretory and Anti–Ulcer Activities of Some New 2–(2–Pyridylmethyl–Sulfinyl)–Benzimidazoles," Eur. J. Med. Chem., (1987) 22:527–37.

Chaney, M.O., et al., "Crystal Parameters For Antibiotic A23187," J. Am. Chem. Soc., (1974) 96:1933.

Chem. Abstr., (1981) 95:692.

Chikashita, H., et al., "In Situ Generation And Synthetic Application Of 2–Phenylbenzimidazoline to the Selective Reduction Of Carbon–Carbon Double Bonds Of Electron–Deficient Olefins," Bull. Chem. Soc. Jpn., (1987) 60:737–46.

David, L., et al., "Production By Controlled Biosynthesis Of A Novel Ionophore Antibiotic, Cezomycin (Demethylamino A23187)," J. Antibiotic., (1982) 35(10):1409–11.

Dunwell, D.W., et al., "Synthesis And Antiinflammatory Activity Of Some 2–Heteroaryl–a–Methyl–5–Benzoxazoleacetic Acids," J. Med. Chem., (1975) 18(11):1158–9.

Dunwell, D.W., et al., "2–Aryl–5–Benzoxazolealkanoic Acid Derivatives With Notable Antiinflammatory Activity," J. Med. Chem., (1975) 18(1):53–58.

Dunwell, D.W., et al., "Synthesis And Antiinflammatory Activity Of Some 2–Aryl–6–Benzoxazoleactic Acid Derivatives," J. Med. Chem. (1977) 20(6):797–801.

Edwards, P.D., et al., "Peptidyl a–Ketoheterocyclic Inhibitors Of Human Neutrophil Elastase. In Vitro And In Vivo Potency Of A Series Of Peptidyl α–Ketobenzoxazoles," J. Med. Chem., (1995) 38:3972–82.

Edwards, P.D., et al., "Design, Synthesis, and Kinetic Evaluation Of A Unique Class Of Elastase Inhibitors, the Peptidyl α–Ketobenzoxazoles, and the X–Ray Crystal Structure of the Covalent Complex Between Porcine Pancreatic Elastase and Ac–Ala–Pro–Val–2–Benzoxazole," J. Am. Chem. Soc. (1992) 114:1854–63.

(List continued on next page.)

*Primary Examiner*—Bennett Celsa
*Assistant Examiner*—Grace Hsu
(74) *Attorney, Agent, or Firm*—Morrison & Foerster, LLP (57) ABSTRACT

The present invention provides an efficient and versatile method for the synthesis and screening of combinatorial libraries of benzimidazoles, benzoxazoles, benzothiazoles, and derivatives thereof. In order to expedite the synthesis of large arrays of compounds possessing these core structures, a general methodology for solid phase synthesis of these derivatives is provided. Arrays of benzimidazoles, benzoxazoles, benzothiazoles, and derivatives thereof useful as peptidomimetics and for the identification of agents having antifungal, antiviral, antimicrobial, anticoagulant, and antiulcer activity, or use in the treatment of inflammation, hypertension, cancer, and other conditions can be prepared by this method.

15 Claims, 2 Drawing Sheets

OTHER PUBLICATIONS

Edwards, P.D., et al., "Peptidyl α–Ketoheterocyclic Inhibitors Of Human Neutrophil Elastase. Effect of Varying the Heterocyclic Ring on In Vitro Potency," J. Med. Chem., (1995) 38:76–85.

Evans, D., et al., "Synthesis and Antiinflammatory Activity Of Some 2–Substituted 4– and 7–Benzoxazoleacetic and α–Methylacetic Acids," J. Med. Chem., (1977) 20(1):169–71.

Haugwitz, R.D., et al., "Antiparasitic Agents. 3. Synthesis And Anthelmintic Activities Of Novel 2–Pyridinyl–5–isothiocyanatobenzimidazoles," J. Med. Chem., (1979) 22(9):1113–8.

Haugwitz, R.D., et al., "Antiparasitic Agents. 5. Synthesis and Anthelmintic Activities Of Novel 2–Heteroaromatic–Substituted Isothiocyanatobenzoxazoles And Benzothiazoles," J. Med. Chem., (1982) 25:969–74.

Hermkens, P.H.H., et al., "Solid–Phase Organic Reactions: A Review of the Recent Literature," Tetrahedron, (1996) 52(13):4527–54.

Hunger, A., et al., "Synthese Basisch Substituierter Analgetisch Wirksamer Benzimidazol–Derivate," Experientia, (1957) 13:400–1.

Janssens, et al., "27–Heterocycles," Chem. Abstr., (1981) 94(5):30580.

Jerchel, D., et al., "Zur Darstellung Der Benzimidazole," Liebigs Annalen Der Chemie, (1952) 575:162–73.

Jung, G., et al., "Organic Chemistry On Solid Supports," Angew. Chem. Int. Ed. Engl., (1996) 35:17–42.

Katsura, Y., et al., Studies On Antiulcer Drugs. II. Synthesis And Antiulcer Activities Of Imidazo [1,2–a]pyridinyl–2–alkylaminobenzoxazoles And 5,6,7,8–Tetrahydroimidazo[1,2–a]pyridinyl Derivatives, Chem. Pharm. Bull., (1992) 40(2):371–80.

Katsura, Y., et al., "Studies On Antiulcer Drugs. III. Synthesis And Antiulcer Activities Of Imidazo[1,2–a]pyridinylethyl–benzoxazoles And Related Compounds. A Novel Class Of Histamine $H_2$–Receptor Antagonists," Chem. Pharm. Bull., (1992) 40(6):1424–38.

Kugishima, H., et al., "Synthesis of 3–[[(2–Benzimidazolyl)thio]methyl]–1–methyl–1,8–dihydrocycloheptapyrazol–8–ones," J. Heterocyclic Chem., (1994) 31:1557–9.

Kusumi, T., et al., "Structure Of The Novel Antibiotics Boxazomycins A, B, and C," J. Am. Chem. Soc., (1988) 110:2954–8.

Mayer, J.P., et al., "Solid–Phase Synthesis Of Benzimidazoles," Tetrahedron Lett., (1998) 39:6655–8.

Meyers, H.V., et al., "Multiple Simultaneous Synthesis Of Phenolic Libraries," Molecular Diversity, (1995) 1:13–20.

Nefzi, A., et al., "The Current Status of Heterocyclic Combinatorial Libraries," Chem. Rev., (1997) 97:449–72.

Pätzold, F., et al., "Dehydrogenations Using Benzofuroxan As Oxidant," Synth. Commun., (1992) 22(2):281–8.

Phillips, G.B., et al., "Solid Phase Synthesis Of Benzimidazoles," Tetrahedron Lett., (1996) 37(28): 4887–90.

Preston, P.N., "Synthesis Of Benzimidazoles," Benzimidazoles and Congeneric Tricyclic Compounds, (1981) 40(1):6–60.

Rastogi, R., et al., "2–Aminobenzimidazoles in Organic Syntheses," Synthesis, (1983) 861–62.

Saluja, S., et al., "Structure–Activity Relationships Among 2–Substituted 5,6–Dichloro–, 4,6–Dichloro–, and 4,5–Dichloro–1–[(2–hydroxyethoxy)methyl]– and –1[(1,3–dihydroxy–2–propoxy)methyl]benzimidazoles," J. Med. Chem., (1996) 39(4):881–891.

Sun, Q., et al., "Single Bead IR Monitoring Of A Novel Benzimidazole Synthesis," Bioorg. Med. Chem. Lett., (1998) 8:361–4.

Suto, M.J., et al., "Synthesis Of Boxazomycin B And Related Analogs," Tetrahedron Lett., (1995) 36(40):7213–6.

Thompson, L. A., et al., "Synthesis and Applications of Small Molecule Libraries," Chem. Rev., (1996) 96:555–600.

Vanden Eynde, J.J., et al., "2,3–Dichloro–5,6–Dicyano–1,4–Benzoquinone, a Mild Catalyst for the Formation of Carbon–Nitrogen Bonds," Tetrahedron, (1995) 51(20):5813–8.

Wang, F., et al., "Solid–Phase Synthesis Of Benzoxazoles via Mitsunobu Reaction," Tetrahedron Lett., (1997) 38(37):6529–32.

Westly, J.W., et al., "Isolation and Characterization Of A Novel Polyether Antibiotic of the Pyrrolether Class, Antibiotic X–14885A," J. Antibiotics, (1983) 36(10):1275–8.

Yadagiri, B., et al., "Convenient Routes To Substituted Benzimidazoles and Imidazolo[4,5–b]Pyridines Using Nitrobenzene As Oxidant," Synth. Commun., (1990) 20(7):955–63.

* cited by examiner

METHODS FOR THE SOLID PHASE SYNTHESIS OF COMBINATORIAL LIBRARIES OF BENZIMIDAZOLES BENZOXAZOLES BENZOTHIAZOLES AND DERIVATIVES THEREOF

This application claims priority to U.S. Provisional Serial Application No. 60/085,465 filed May 4, 1998, the contents of which are incorporated herein by reference.

TECHNICAL FIELD

The present invention provides a method for the combinatorial synthesis and screening of libraries of benzimidazoles, benzoxazoles, benzothiazoles, and derivatives thereof. In order to expedite the synthesis of compound libraries possessing these core structures, the present invention also provides a general method for the solid phase synthesis of benzimidazoles, benzoxazoles, benzothiazoles, and derivatives thereof. The method involves a cyclization reaction between a 1,2-arylenediamine, 2-aminophenol, or 2-aminothiophenol and an aldehyde or cyanogen bromide, respectively. Either the 1,2-arylenediamine, 2-aminophenol, or 2-aminothiophenol component, or the aldehyde component, may be covalently attached to the solid support.

BACKGROUND ART

The synthesis and screening of small molecule combinatorial libraries is an important tool in drug discovery. A convenient format for the generation of these libraries is the preparation of compounds on a solid support Solid-phase organic synthesis (SPOS) is especially useful for many synthetic transformations, since reagents can be used in large excess to drive reactions to completion, and any unreacted amount of reagents and soluble byproducts can be easily removed by filtration (see Thompson and Ellman 1996, Chem. Rev. 96:555.; Herkens et al. 1996, Tetrahedron 52:4527; Früchtel and Jung 1996, Angew. Chem. Int. Ed. Engl. 35:17–42; Balkenhold et al. 1996, Angew. Chem. Int Ed Engl. 35:2288–2337).

Substituted heterocyclic compounds offer a high degree of molecular diversity and have proven to be broadly useful as therapeutic agents. The benzimidazole, benzoxazole, and benzothiazole ring systems, in particular, are present in many known herbicides, fungicides, and drugs used in human as well as veterinary medicine. The generic structure and numbering system of these compounds are shown below.

Benzimidazole    Benzoxazole    Benzothiazole

Benzimidazoles, benzoxazoles, and benzothiazoles have been shown to exhibit antiviral (Salluja et al. 1996, J. Med. Chem. 39:881–891), antiulcer (Cereda et al. 1987, Eur. J. Med. Chem. 22:527–537; Kugishima et al. 1994, Heterocyclic Chem. 31:1557–1559.), antihistaminic (Jerchee et al. 1952, Liebigs Annalen der Chemie 575:173; Janssens at al. 1981, Chem. Abstr. 94:30579), analgesic (Hunger at al. 1957, Experientia 13:400), antihelmintic (Gyurik et al. 1981, U.S. Pat. No. 4,258,198; 1981, Chem Abstr. 95:7284), antibacterial (Kusumi et al. 1988, J. Am. Chem. Soc. 110:2954; Suto et al. 1995, Tetrahedron Lett. 36:7213; Chaney et al. 1974, J. Am. Chem. Soc. 96:1932; David et al. 1982, J. Antibiotic. 35:1409; Westly et al. 1983, J. Antibiotic. 36:1275), antiparasitic (Haugwitz et al. 1979, J. Med. Chem. 22:1113; Haugwitz et al. 1982, J. Med. Chem. 25:969), and antiinflammatory properties (Dunwell et al. 1975, J. Med. Chem. 18:53; Dunwell et al. 1975, J. Med. Chem. 18:1158; Evans et al. 1977, J. Med. Chem. 20:169; Dunwell et al. 1977, J. Med. Chem. 20:797), or other biologically relevant actions such as inhibition of elastase (Edwards et al. 1992, J. Am. Chem. Soc. 114:1854; Edwards et al. 1995, J. Med. Chem. 38:87; Edward et al. 1995, J. Med. Chem. 38:3972), and $H_2$-antagonist properties (Katsura et al. 1992, Chem. Pharm. Bull. 40:371; Katsura et al. 1992, Chem. Pharm. Bull. 40:1424).

In spite of their importance as phannacophoric scaffolds, there has been a lack of mild and efficient techniques for synthesizing benzimidazoles, benzoxazoles, and benzothiazoles on a solid support and, particularly, for producing libraries of derivatives for biological screening. Thus, the development of strategies for the solid phase synthesis of these heterocyclic systems and derivatives thereof is not only highly desirable, but also economically advantageous (see Nefzi et al. 1997, Chem. Rev. 97:449–472).

Benzimidazoles, benzoxazoles, and benzothiazoles are usually prepared in solution by heating a 1,2-arylenediamine, 2-aminophenol, or 2-aminothiophenol with carboxylic acids or their derivatives (chlorides, anhydrides, esters, amides, imino esters) at elevated temperatures and/or in the presence of strong acids (see Preston, P. N. Benzimidazoles and Congeneric Tricyclic Compounds. In Heterocyclic Compounds; Preston, P. N., Ed.; John Wiley & Sons, NY, 1981, Vol. 40, pp 6–60). These conditions, however, are not always suitable for solid phase organic synthesis, particularly when thermally sensitive polymeric supports and/or acid-labile linkers are employed. In spite of this fact, the current methods for the solid phase synthesis of benzimidazoles and benzoxazoles are for the most part based on the above general approach and, therefore, subjected to its limitations. For example, Phillips and Wei (Tetrahedron Lett. 37 (1996) pp.4887–4890) disclose a process for the solid phase synthesis of benzimidazoles that includes heating an immobilized 1,2-arylenediamine with an imino ester. Although the use of an imino ester allows one to carry out the reaction under essentially neutral conditions, a large excess of the reagent (ca. 30 eq.) and prolonged heating (ca. 55–90° C. for 24–40 h) are still needed to induce heterocycle ring formation. Imino esters, on the other hand, are not readily available reagents and must be individually prepared, isolated, and purified by conventional methods before they can be used in the synthesis of combinatorial libraries.

Wang and Hauske (Tetrahedron Lett. 38 (1997) pp.6529–6532) disclose a method for the solid phase synthesis of benzoxazoles that involves a two-step reaction, in which a carboxylic acid is first amidated with a 2-aminophenol, and the resulting amidophenol is then cyclized intramolecularly. This method relies on the selective amidation of the resin-bound carboxylic acid with a 2-aminophenol without concomitant esterification, and in the intramolecular nature of the process.

Benzimidazoles have also been obtained in solution by treatment of a 1,2-arylenediamine with aldehydes and an oxidizing agent (see Chikashita et al. 1987, Bull. Chem. Soc. Jpn. 60:737–746; Yadagiri and Lown 1990, Synth. Commun. 20:955–963; Pätzold et al. 1992, Synth. Commun. 22:281–288; Vanden Eynde et al. 1995, Tetrahedron 51:5813–5818), or by treatment of a 1,2 arylenediamine with cyanogen bromide (see Rastogi and Sharma 1983, *Synthesis* 861–882). Although not as widely publicized as the thermal cyclization of 1,2-arylenediamines with carboxylic acids or their derivatives, these alternative methods are known to afford benzimidazoles under very mild conditions.

A few of these methods have been applied to the solid phase synthesis of benzimidazoles from either immobilized aldehydes (see Sun et al. 1998, *Bioorg. Med. Chem. Lett.* 8:361–364) or immobilized 1,2-arylenediamines (see Mayer et al. 1998, *Tetrahedron Lett.* 39:6655–6658), but not both. In the first case, the oxidizing agent used is nitrobenzene and the reaction is still performed at high temperature (ca. 130° C.); in the second case, the oxidizing agent is DDQ and the reaction is carried out at or near room temperature.

DESCRIPTION OF THE INVENTION

The description of the invention is provided according to the following outline.

OUTLINE

1. Terminology
2. Disclosure of the Invention
2.1. Overview
2.2. The 1,2-Arylenediamine, 2-Aminophenol and 2-Aminothiophenol Component
2.3. The Aldehyde Component
3. The Reaction Conditions
3.1. Immobilization of the Arylenediamine, Aminophenol, Aminothiophenol, or Aldehyde Component
3.2. Reaction of Solid-Supported 1,2-Arylenediamines, 2-Aminophenols, or 2-Aminothiophenols with Cyanogen bromide
3.3. Reaction of Solid-Supported 1,2-Arylenediamines, 2-Aminophenols, or 2-Aminothiophenol with Aldehydes
3.4. Reaction of Solid-Supported Aldehydes with 1,2-Arylenediamines, 2-Aminophenols, or 2-Aminothiophenols
4. Preparation of Derivatives of Benzimidazoles, Benzoxazoles, and Benzothiazoles
5. Cleavage and Analysis of Products
6. Preparation of Arrays of Benzimidazoles, Benzoxazoles, and Benzothiazoles 1. Terminology Unless otherwise stated, the following terms, abbreviations, and pictorial representations used in the description, specifications, and claims of the invention have the meanings given below:

"Alkyl" refers to a straight chain, branched, or cyclic chemical group containing only carbon and hydrogen, such as methyl, —(CH$_2$)—, tert-butyl, and cyclopentyl. Alkyl groups can be either unsubstituted or substituted with one or more substituents, e.g., halogen, hydroxy, alkoxy, amino, mercapto, acyloxy, carboxy, aryl, heteroaryl, or other functionality which may be suitably blocked, if necessary for purposes of the invention, with a protecting group. Typically, alkyl groups will comprise 1 to 12 carbon atoms, preferably 1 to 10, and more preferably 1 to 8 carbon atoms.

"Alkoxy" refers to the group alkyl—O—.

"Aryl" or "Ar" refers to an aromatic carbocyclic group having a single ring (e.g., phenyl) or multiple condensed rings (e.g., naphthyl), which can be either unsubstituted or substituted with alkyl, halogen, hydroxy, alkoxy, mercapto, amino, nitro, cyano, carboxy, and carboalkoxy. Preferred aryl groups include phenyl, 1-naphthyl, 2-naphthyl, biphenyl, and the like.

"Aryloxy" refers to the group aryl—O—.

"Heteroaryl" or "HetAr" refers to a monovalent unsaturated aromatic carbocyclic group having a single ring (e.g, furanyl, pyridyl, thiophenyl) or multiple condensed rings (e.g., benzimidazolyl, indolizinyl) and containing at least one heteroatom, such as N, O, or S, within the ring, which can optionally be unsubstituted or substituted with alkyl, halogen, hydroxy, alkoxy, mercapto, amino, nitro, cyano, carboxy, and other substituents.

"Arylalkyl" refers to the groups —R'—Ar and —R'—HetAr, where R' is an alkyl group, Ar is an aryl group, and HetAr is a heteroaryl group. Examples of arylalkyl groups include benzyl (Bn) and furfuryl.

"Amino" or "amine" refers to the group —NR'R", where R' and R" are independently selected from the group consisting of hydrogen, alkyl, aryl, arylalkyl, and heteroaryl. In a primary amino group, both R' and R" are hydrogen, whereas in a secondary amino group, either, but not both, R' and R" is hydrogen.

"Carboxy" or "carboxyl" refers to the group —COOH.

"Carboalkoxy" refers to the group —COOR', where R' is an alkyl group.

"Carboaryloxy" refers to the groups —COOAr and —CO—HetAr, where Ar is an aryl group and HetAr is a heteroaryl group.

"Carboalkyl" refers to the group —CO—R', where R' is an alkyl group.

"Carboaryl" refers to the groups —CO—Ar and —CO—HetAr, where Ar is an aryl group and HetAr is a heteroaryl group.

"Chemical library" or "combinatorial library" or "compound library" or "array" is an intentionally created collection of different compounds, usually prepared in parallel, and screened for biological activity in a variety of different formats (e.g., in solution or tethered to resin beads, silica chips, or other solid supports).

"Building block" refers to any molecule that can be covalently attached to other molecules to generate structurally different compounds.

"Combinatorial chemistry" or "combinatorial synthesis" refers to an ordered strategy for the parallel synthesis of diverse molecular entities which leads to the generation of chemical libraries. The strategy consists of the systematic and repetitive covalent connection of structurally different building blocks to each other to yield large arrays of compounds.

"Linker" refers to a molecule or group of molecules covalently attached to the solid support on one end and to the first building block on the other end. Linkers have different molecular structures and, therefore, different lengths, shapes, sizes, degree of hydrophobicity and hydrophilicity, steric bulk, and chemical reactivity. The selection of a linker in solid phase synthesis is dependent on both the synthetic scheme and the biological screening format.

"Solid support" refers to a material or group of materials having a rigid or semi-rigid surface, appropriate size, shape, and porosity, and high chemical resistance. Examples of solid supports are glass, silica, cellulose, polystyrene crosslinked with divinylbenzene, polystyrene-polyethyleneglycol copolymer, and other support materials commonly used in peptide, polymer, and small-molecule solid phase synthesis.

"Resin" refers to a solid support material which has been grafted with a linker for attachment of the first building block. Examples of preferred resins are Wang resin (a polystyrene-based resin with a 4-alkoxybenzyl alcohol linker), Rink amide resin (a polystyrene-based resin with a 4-(2',4'-dimethoxyphenylaminomethyl)phenoxymethyl linker), and Sasrin resin (a polystyrene-based resin with a 2-methoxy4-alkoxybenzyl alcohol linker). Other preferred resins are described in the *Combinatorial Chemistry & Solid Phase Organic Chemistry Handbook* published by NovaBiochem, La Jolla, Calif.; the *Solid Phase Sciences* catalog published by Solid Phase Sciences, San Rafael, Calif., or the *Rapp Polymere* catalog published by Rapp Polymere GmbH, Tubingen, Germany.

Resins are usually depicted as follows:

Immobilization of a building block onto a resin is usually depicted as follows:

wherein the type of functional group used for attachment will depend on the nature of both the compound to be synthesized and the resin employed.

"Protecting group" or "PG" refers to a chemical group that exhibits the following characteristics: (a) reacts selectively with the desired functionality to give a derivative that is stable to the ensuing reactions to which it will be subjected; (b) can be selectively removed from the derivative to afford the desired functionality in good yield, and (c) the conditions for its removal do not compromise the integrity of other functional groups.

Examples of protecting groups can be found in Greene et al. 1991, *Protective Groups in Organic Synthesis,* 2nd. Ed., John Wiley & Sons, Inc., New York.

Abbreviations: The following abbreviations are intended to have the following meaning:

API=Atmospheric Pressure Ionization
DCC=Dicyclohexylcarbodide
DCM=Dichloromethane
DIC=Diisopropylcarbodiimide
DIEA=Diisopropylethylamine
DMA=Dimethylacetamide
DMAP=4-Dimethylaminopyridine
DMF=Dimethylformamide
DMSO=Dimethylsulfoxide
ES=Electrospray
EtOH=Ethanol
Fmoc=Fluorenylmethoxycarbonyl
HBTU=O-Benzotriazol-1-yl-N,N,N',N'-tetramethyluronium hexafluorophosphate
HOBt=1-Hydroxybenzotriazole
HPLC=High-Performance Liquid Chromatography
MeCN=Acetonitrile
MeOH=Methanol
MS=Mass Spectrum
MSNT=1-(Mesitylene-2-sulfonyl)3-nitro-1,2,4-triazole
NMI=1-Methylimidazole
NMR=Nuclear Magnetic Resonance
PG=Protecting group
SPOS=Solid Phase Organic Synthesis
TBTU=O-Benzotriazol-1-yl)-N,N,N',N'-tetramethyluronium tetrafluoroborate
TCNE=Tetracyanoethylene
TEA=Triethylamine
TFA=Trifluoroacetic acid
THF=Tetrahydrofuran

2. Disclosure of the Invention 2.1. Overview

The present invention discloses an efficient and versatile approach for the combinatorial synthesis and screening of libraries of benzimidazoles, benzoxazoles, benzothiazoles, and derivatives thereof. In order to expediently synthesize a combinatorial library of benzimidazoles, benzoxazoles, benzothiazoles, and derivatives thereof, a generalized methodology for the solid phase synthesis of these compounds is also provided. This methodology overcomes the limitations of previous approaches for the solid phase synthesis of benzimidazoles and benzoxazoles, and provides the first example of a solid phase synthesis of benzothiazoles.

In one aspect of the invention, the method of synthesizing benzimidazoles, benzoxazoles, benzothiazoles, and derivatives thereof, comprises the steps of first immobilizing a 1,2-arylenediamine, 2-aminophenol, 2-aminothiophenol, or a synthetic precursor thereof, onto a solid support; removing any protecting groups or performing other operations upon said synthetic precursor to unmask the amino, hydroxy, and mercapto functionalities, and fretting the resulting 1,2-arylenediamine, 2-aminophenol, or 2-aminothiophenol with cyanogen bromide to form the corresponding heterocycles, which is depicted below:

Reaction 1

-continued

In "Reaction 2", the resin-bound 1,2-arylene diamine can be attached to the solid support through a linker off the aromatic ring as shown in the scheme (first reaction), or through a substituent off one of the nitrogens as shown below:

In another aspect of the invention, the method of synthesizing benzimidazoles, benzoxazoles, benzothiazoles, and derivatives thereof, comprises the steps of first immobilizing a 1,2-arylenediamine, 2-aminophenol, 2-aminothiophenol, or a synthetic precursor thereof, onto a solid support; removing any protecting groups or performing other operations upon said synthetic precursor to unmask the amino, hydroxy, and mercapto functional groups, and treating the resulting 1,2-arylenediamine, 2-aminophenol, or 2-aminothiophenol, either sequentially or simultaneously, with an aldehyde and an oxidizing agent to form the corresponding heterocycles, which is depicted as follows:

Reaction 2

In yet another aspect, the method of synthesizing benzimidazoles, benzoxazoles, benzothiazoles, and derivatives thereof, comprises the steps of first immobilizing an aldehyde, or a synthetic precursor thereof, onto a solid support, removing any protecting groups or performing other operations upon said synthetic precursor to unmask the aldehyde functional group, and treating the resulting aldehyde, either sequentially or simultaneously, with an 1,2-arylenediamine, 2-aminophenol, or 2-aminothiophenol and an oxidizing agent to form the corresponding heterocycles, which is depicted as follows:

Reaction 3

-continued

2.2. The 1,2-Arylenediamine, 2-Aminophenol, and 2-Aminothiophenol Component

According to the above embodiments, the 1,2-arylenediamine, 2-aminophenol, and 2-aminothiophenol component preferably comprises compounds of formula I, II, and III, respectively:

Formula wherein $R_1$ is selected from the group consisting of hydrogen, alkyl, halogen, hydroxy, alkoxy, aryloxy, amino, carboxy, carboalkoxy, cyano, and nitro, and $R_2$ is selected from the group consisting of alkyl, aryl, heteroaryl, arylalkyl, or substituted arylalkyl.

Depending on the combinatorial or synthetic scheme, the 1,2-arylenediamine, 2-aminophenol, and 2-aminothiophenol component may contain additional substituents on the phenyl ring. If necessary, these substituents can be protected with an appropriate protecting group.

In a more preferred embodiment, the 1,2-arylenediamine, 2-aminophenol, and 2-aminothiophenol component is selected from the group consisting of, but not limited to, 1,2-phenylenediamine; N-methyl-1,2-phenylenediamine; 2,3-diaminonitrobenzene; 3,4-diaminobenzoic acid; 3-amino4N-benzylamino)benzoic acid; 2,3-diaminophenol; 3,4-diaminophenol; 2-aminophenol; 3-amino4hydroxybenzoic acid; 4-amino-3-hydroxy-benzoic acid; 2-aminothiophenol; 3-amino mercaptobenzoic acid; 4-amino-3-mercapto-benzoic acid. The 1,2-arylenediamine, 2-aminophenol, and 2-aminothiophenol component, if not commercially available, can be prepared by standard chemical procedures.

2.3. The Aldehyde Component

According to the above embodiments, the aldehyde component preferably comprises a compound of formula IV, V, or VI:

Formula wherein $R_3$ is an alkyl or arylalkyl group, Ar is an aryl group, and HetAr is a heteroaryl group, either unsubstituted or preferably substituted with one or more substituents selected from the group consisting of alkyl, halogen, hydroxy, alkoxy, mercapto, amino, nitro, cyano, carboxy, and carboalkoxy. If necessary, these substituents can be protected with an appropriate protecting group.

In a more preferred embodiment, the aldehyde component is selected from the group consisting of, but not limited to, benzaldehyde; 2-formylbenzenesulfonic acid; 5-formyl-2-furansulfonic acid; 4-fluorobenzaldehyde; 2-hydroxybenzaldehyde; 3-hydroxybenzaldehyde; 4-hydroxybenzaldehyde; 3,4dihydroxybenzaldehyde; 3,5-dihydroxybenzaldehyde; 2-nitrobenzaldehyde; 4-nitrobenzaldehyde; 4-dimethyl-aminobenzaldehyde; 4-hydroxy-3-nitrobenzaldehyde; 5-nitro-2-furaldehyde; 5-nitro-2-thiophenecarboxaldehyde; 2-carboxybenzaldehyde; 3-carboxybenzaldehyde; 4-carboxy-benzaldehyde; 4-formylcinnamic acid. The aldehyde component, if not commercially available, can be prepared by standard chemical procedures.

3. The Reaction Conditions

3.1. Immobilization of the Arylenediamine, Aminophenol, Aminothiophenol, or Aldehyde Component According to the present invention, a 1,2-arylenediamine, 2-aminophenol, or 2-aminothiophenol component is reacted with either cyanogen bromide or an aldehyde component and an oxidant component, to yield a benzimidazole, benzoxazole, benzothiazole, or a derivative thereof. The 1,2-arylenediamine, 2-aminophenol, or 2-aminothiophenol component, or the aldehyde component, can be utilized in a soluble format or can be attached to a solid support.

According to the latter embodiment, the 1,2-arylenediamine, 2-aminophenol, or 2-aminothiophenol component, or the aldehyde component, will include a functionality which can covalently bind the molecule to the solid support. This functionality will be present in the molecule in addition to the 1,2-diamino, 2-amino-1-hydroxy, or 2-amino-1-mercapto groups, or to the aldehyde group, or protected derivatives or synthetic precursors thereof.

The choice of functionality used for attaching the 1,2-arylenediamine, 2-amino-phenol, or 2-aminothiophenol component, or the aldehyde component, to the solid support will depend on the nature of the compound to be synthesized and the type of resin employed. Preferred functionalities include, but are not limited to, halogen, hydroxy, amino, and carboxy. Conditions for coupling monomers and polymers to solid supports through these functional groups are known in the art; illustrative examples are given in reaction scheme 4.

Reaction 4

-continued

3.2. Reaction of Solid-Supported 1,2-Arylenediamines, 2-Aminophenols, or 2-Aminothiophenols with Cyanogen bromide In a preferred embodiment, an immobilized 1,2-arylenediamine, 2-aminophenol, or 2-aminothiophenol component is treated with a solution of cyanogen bromide, usually at ambient temperature, and for a period of 2 to 24 h. However, depending on the nature of the components, those skilled in the art will recognize that it may be necessary to perform the reaction at temperatures other than ambient and for periods of time longer than 24 h.

The reaction is typically performed in an organic solvent, such as acetonitrile, dichloromethane, tetrahydrofuran, methanol, aqueous methanol, dimethylformamide, or dimethylacetamide. Most preferably, acetonitrile and dichloromethane are used. The ratio of 1,2-arylenediamine, 2-aminophenol, or 2-aminothiophenol component to cyanogen bromide component will typically range from about 1:1.1 to about 1:100, preferably from about 1:1.1 to about 1:25.

Hydrogen bromide is formed as a secondary product of the reaction. In some instances, it may be necessary to neutralize the hydrogen bromide formed by addition of an exogenous base. In a preferred embodiment, the exogenous base will be soluble in the reaction solvent. Particularly preferred exogenous bases include tri(lower alkyl)amines, such as diisopropylethylamine (DIEA) or triethylamine (TEA).

3.3. Reaction of Solid-Supported 1,2-Arylenediamines, 2-Aminophenols, or 2-Aminothiophenols with Aldehydes In a preferred embodiment, an immobilized, 2-arylenediamine, 2-aminophenol, or 2-aminothiophenol component is treated, either sequentially or simultaneously, with an aldehyde component and an oxidant component, usually at ambient temperature, and for a period of 2 to 24 h. However, depending on the nature of the components, those skilled in the art will recognize that it may be necessary to perform the reaction at temperatures other than ambient and for periods of time longer than 24 h.

The oxidant employed in the reaction is selected from a group consisting of p-chloranil (CA); 7,7,8,8-tetracyanoquinodimethane (TCNQ); benzylidenemalononitrile (BMCN); tetracyanoethylene (TCNE); 2,3-dicyano-1,4-benzoquinone (DCBQ), or 2,3-dichloro-5,6-dicyano-1,4-benzoquinone (DDQ). Most preferably, TCNE is used.

The ratio of 1,2-arylenediamine, 2-aminophenol, or 2-aminothiophenol component to aldehyde component and to oxidant component will typically range from about 1:1.1:1.1 to about 1:100:100, preferably from about 1:1.1:1.1 to about 1:25:25, and most preferably from about 1:1.1:1.1 to about 1:10:10.

The reaction is typically performed in an organic solvent, such as tetrahydrofuran, dichloromethane, methanol, , acetonitrile, dimethylformamide, dimethylacetamide, or combinations thereof Most preferably, dichloromethane and dimethylacetamide are used.

In some instances, the reaction is performed in the presence of a dehydrating agent which is some embodiments may serve to catalyze the condensation reaction. Preferred dehydrating agents include molecular sieves, magnesium sulfate, trimethyl orthoformate, and the like.

3.4. Reaction of Solid-Supported Aldehydes with 1,2-Arylenediamines, 2-Aminophenols, or 2-Aminothiophenols In a preferred embodiment, an immobilized aldehyde is treated, either sequentially or simultaneously, with a 1,2-arylenediamine, 2-aminophenol, or 2-aminothiophenol component and an oxidant component, usually at ambient temperature, and for a period of 2 to 24 h. However, depending on the nature of the components, those skilled in the art will recognize that it may be necessary to perform the reaction at temperatures other than ambient and for periods of time longer than 24 h.

The oxidant employed in the reaction is selected from a group consisting of p-chloranil (CA); 7,7,8,8-tetracyanoquinodimethane (TCNQ); benzylidenemalononitrile (BMCN); tetracyanoethylene (TCNE); 2,3-dicyano-1,4-benzoquinone (DCBQ), or 2,3-dichloro-5,6dicyano-1,4-benzoquinone (DDQ). Most preferably, TCNE is used.

The ratio of aldehyde component to 1,2-arylenediamine, 2-aminophenol, or 2-aminothiophenol component and to oxidant component will typically range from about 1:1.1:1.1 to about 1:100:100, preferably from about 1:1.1:1.1 to about 1:25:25, and most preferably from about 1:1.1:1.1 to about 1:10:10.

The reaction is typically performed in an organic solvent, such as tetrahydrofuran, dichloromethane, methanol, ethanol, acetonitrile, dimethylformamide, dimethylacetamide, or combinations thereof. Most preferably, dichloromethane and dimethylacetamide are used.

In some instances, the reaction is performed in the presence of a dehydrating agent which is some embodiments may serve to catalyze the condensation reaction. Preferred dehydrating agents include molecular sieves, magnesium sulfate, trimethyl orthoformate, and the like.

4. Preparation of Derivatives of Benzimidazoles, Benzoxazoles, and Benzothiazoles The benzimidazoles, benzoxazoles, or benzothiazoles prepared according to the method described in the present invention can be further manipulated using any one or more of a variety of transformations to increase the molecular diversity of the final products.

Figure 1:
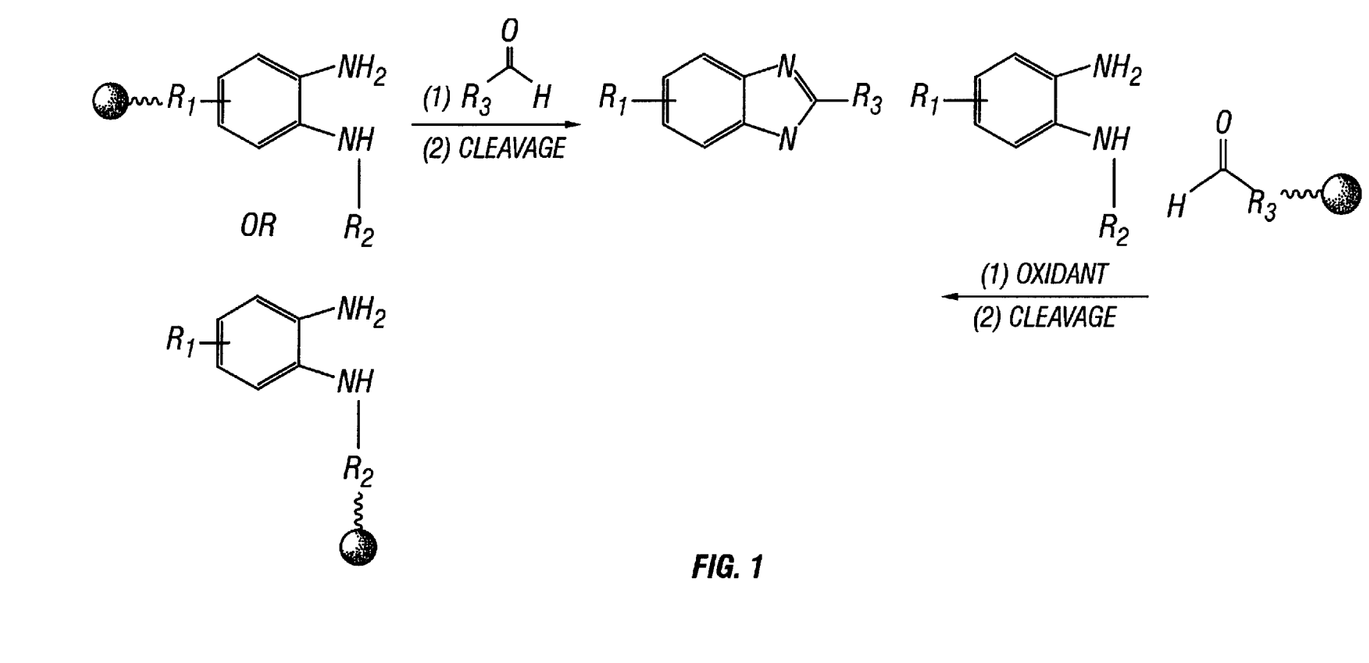
FIG. 1 illustrates the versatility of our approach towards benzimidazoles, in particular, the preparation from either resin-bound diamines or resin-bound aldehydes. This enhances molecular diversity of the combinatorial libraries that may be prepared.
Figure 2:
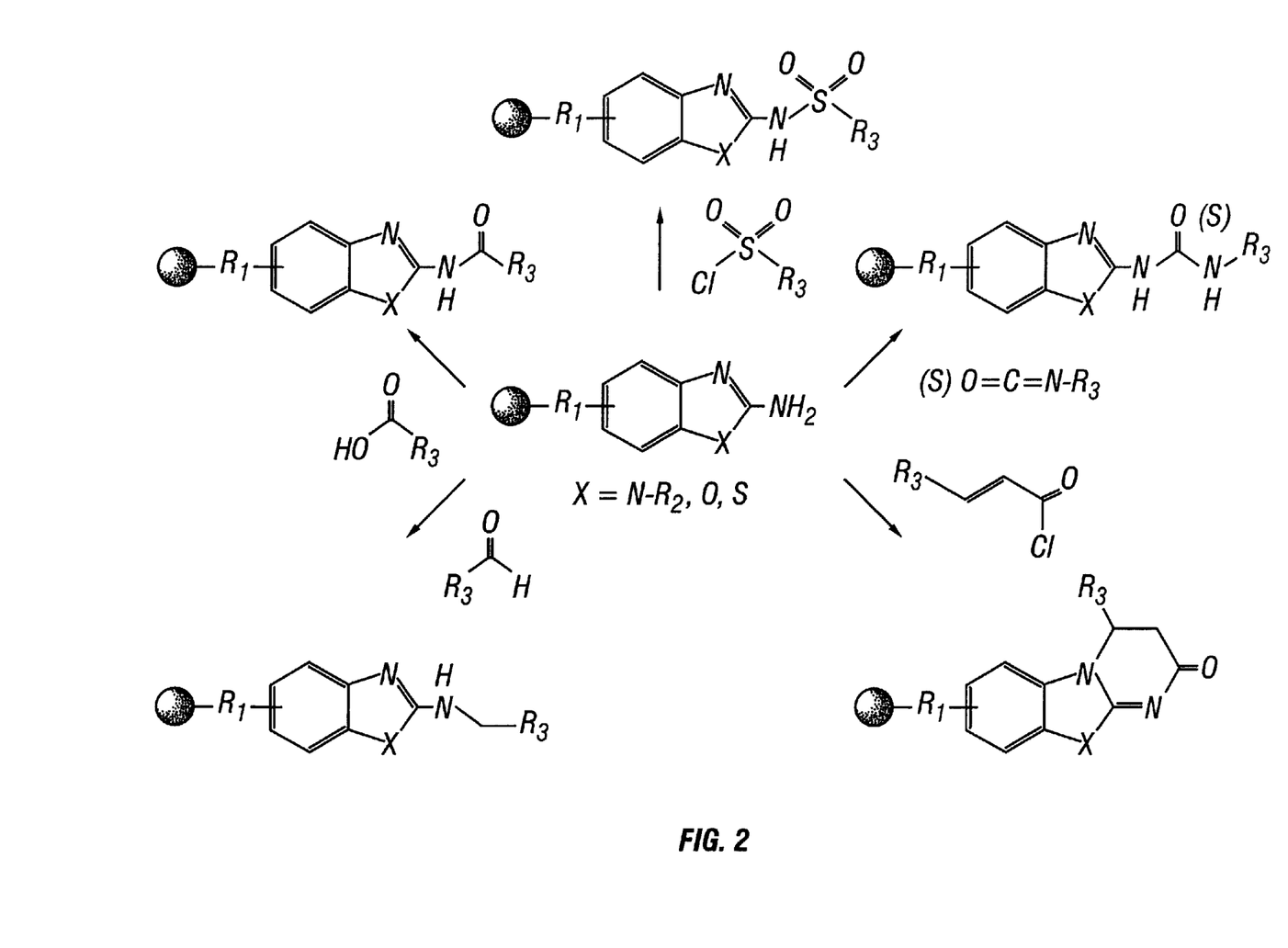
FIG. 2 illustrates the possible reactions associated with a multi-step process for creating diverse libraries.

For example, the 2-amino group of the benzimidazoles, benzoxazoles, or benzothiazoles formed in the reaction of 1,2-arylenediamines, 2-aminophenols, or 2-aminothiophenols with cyanogen bromide, respectively, can be acylated with carboxylic acids or their acyl derivatives (e.g., chlorides or anhydrides) to form amides; sulfonylated with sulfonyl chlorides to form sulfonamides; reacted with isocyanates or isothiocyanates to form ureas or thioureas; condensed with α,β-unsaturated carboxylic acid chlorides or esters to yield fused 2-oxo-pyrimidyl derivatives, or alkylated with aldehydes in the presence of a reducing agent (e.g., NaBH$_4$, NaCN(BH$_3$), Na(OAc)$_3$BH), to give secondary amines. These examples are illustrated in FIG. 1. Other preferred transformations of 2-aminobenzimidazoles, which may be applied to their congeneric heterocyclic compounds, are described in Rastogi and Sharma 1983, Synthesis 861–882.

The above examples are illustrative; other transformations, such as oxidation of the sulfur atom of benzothiazoles, alkylation of the heterocyclic nitrogens of benzimidazoles, and the like, will be apparent to those skilled in the art.

For purposes of simplicity, FIG. 1 shows benzimidazoles, benzoxazoles, and benzothiazoles obtained from resin-bound 1,2-arylenediamines, 2-aminophenols, or 2-aminothiophenols and cyanogen bromide; however, the corresponding benzimidazoles, benzoxazoles, or benzothiazoles obtained from resin-bound 1,2-arylenediamines, 2-aminophenols, or 2-aminothiophenols and aldehydes, or from resin-bound aldehydes and 1,2-arylenediamines, 2-aminophenols, or 2-aminothiophenols can also be further derivatized.

5. Cleavage and Analysis of Products

For some applications, it may be desirable to have a "support-free" or "soluble" library of molecules. Soluble molecules can be useful for a variety of purposes, including structural analysis and screening for activity in a particular assay. The generation of support-free molecular libraries and the solubilization of compounds synthesized on a solid support can be accomplished by techniques known in the art.

Typically, the linkers employed to immobilize a molecule to a solid support can be cleaved under a variety of conditions, including treatment with acid, base, nucleophiles (ie., groups capable of donating electrons), oxidants, reducing agents, and light. Examples of resins with cleavable linkers are described in the *Combinatorial Chemistry & Solid Phase Organic Chemistry Handbook* published by NovaBiochem, La Jolla, Calif.

In a preferred embodiment, acid-sensitive linkers such as those present in Wang resin, Sasrin resin, and Rink amide resin can be employed in the solid phase synthesis of benzimidazoles, benzoxazoles, benzothiazoles, and derivatives thereof, described in the present invention. Thus, if desired, the immobilized products can be cleaved from the solid support by treatment with an acid, and the support-free benzimidazoles, benzoxazoles, benzothiazoles, and derivatives thereof, released into solution.

The nature and amount of acid used in the cleavage step will depend on the specific resin employed in the solid phase synthesis, and on the chemical stability of the products. Preferably, the acid will be selected from the group consisting of acetic acid (AcOH), trifluoroacetic acid (TFA), hydrochloric acid (HCl), and hydrofluoric acid (HF). Most preferably, trifluoroacetic acid is used.

The acid is usually employed in solution, with water and dichloromethane being the preferred solvents. The amount of acid in the solution will typically range from about 1% (v/v) to about 95% (v/v), preferably from about 1% (v/v) to about 50% (v/v), and most preferably from about 1% (v/v) to about 25% (v/v).

The support-free benzimidazoles, benzoxazoles, and benzothiazoles, or derivatives thereof, can be analyzed by standard analytical methods, such as thin-layer chromatography (TLC), high-performance liquid chromatography (HPLC), nuclear magnetic resonance spectroscopy (NMR), infrared spectroscopy (IR), and mass spectrometry (MS). Combinatorial libraries are preferably analyzed by a combination of HPLC and MS, herein referred to as "LC/MS," which provides information on the identity as well as the purity of the cleaved products.

6. Preparation of Arrays of Benzimidazoles, Benzoxazoles, and Benzothiazoles

The method for the solid phase synthesis of benzimidazoles, benzoxazoles, benzothiazoles, and derivatives thereof, disclosed in the present invention can be used to prepare and screen large numbers of compounds, in the hundreds, the thousands, and even in the ten thousands in a reasonable period of time. Synthesis may be coordinated with screening in various different ways to assay compounds from unusually large libraries in a timely manner.

Accordingly, the method of synthesis described above is preferably used to prepare more than 2, preferably more than 10, preferably more than 40, and more preferably more than 90 different compounds simultaneously. Moreover, the method described herein can be utilized in a stepwise fashion as well as in a one step condensation reaction, thereby decreasing significantly the number of reactions required for the preparation of a combinatorial library. For example, a 288-component library can be readily prepared in one step by condensing a solid supported 1,2-arylenediamine, a 2-aminophenol, and a 2-aminothiophenol each with a set of 96 different aldehydes under the conditions described in this invention. Alternatively, a 288-component combinatorial library can be prepared in two steps by condensing a solid supported 1,2-arylenediamine, a 2-aminophenol, and a 2-aminothiophenol each with cyanogen bromide under the conditions described in this invention, and then reacting the 2-aminobenzimidazole, 2-aminobenzoxazole, or 2-aminobenzothiazole with 96 different carboxylic acids or their acyl derivatives. The 2-aminobenzimidazole, 2-amino-benzoxazole, or 2-aminobenzo-thiazole prepared in the first step can also be reacted with different sulfonyl chlorides, isocyanates, thioisocyanates, or aldehydes and a reducing agent, to increase the total number of library components.

Those skilled in the art will recognize the above format as one that can be performed on any array, e.g. 96-well filtration plate, preferably with but also without the aid of automated liquid dispensing equipment.

The method of synthesis of benzimidazoles, benzoxazoles, benzothiazoles, and derivatives thereof, described in the present invention is particularly suitable for the generation of combinatorial libraries because of the following attributes: (a) the synthesis of benzimidazoles, benzoxazoles, benzothiazoles, and derivatives thereof, takes place at room temperature and under neutral conditions; (b) reaction times are usually 1 day or less; (c) most reagents are commercially available; (d) chemical yield and purity of the products are very high, thereby requiring small amounts of solid supported starting material; (e) the oxidative cyclization reaction between 1,2-arylenediamines, 2-aminophenols, or 2-aminothiophenols and aldehydes is highly chemoselective and tolerates a wide range of substituents on either component, which enhances the structural diversity of the compounds that can be prepared by this method; (f) in the oxidative cyclization process, either the 1,2-arylenediamine, 2-aminophenol, or 2-aminothiophenol component, or the aldehyde component, can be immobilized onto the solid support, which also contributes to increase the structural diversity of the compounds that can be prepared by this approach; (g) the method provides a general and uniform protocol for the synthesis of all three classes of heterocycles, ie., benzimidazoles, benzoxazoles, and benzothiazoles. Furthermore, compound libraries possessing these core structures can be prepared from a common resin-bound aldehyde, thereby maximizing the value and efficiency of the synthetic process

EXAMPLES

The following examples are included for the purpose of illustrating the invention and are not intended to limit its scope in any matter.

Example 1

Preparation of Resin-Bound 4-Carboxybenzaldehyde

4-Carboxybenzaldehyde (2.61 g, 17.4 mmol), DCC (2.19 g, 17.4 mmol), HOBt (1.17 g, 8.7 mmol), and DMAP (1.06 g, 8.7 mmol) were dissolved in dry DMA (8.1 mL). The solution was added to Wang resin (15.0 g, subn. 0.58 mmol/g, 8.7 mmol), and the resulting suspension was shaken at room temperature for 24 h. The resin was filtered, washed successively with DMA, DCM, and dried under high vacuum. The loading of the resin was determined by direct cleavage of an aliquot with 20% (v/v) TFA in DCM, and subsequent analysis of the product by HPLC.

Example 2

Preparation of Resin-Bound N,N'-Fmoc-3,4-Diaminobenzoic Acid

A solution of N,N'-Fmoc-3,4-diaminobenzoic acid (3.76 g, 6.3 mmol), MSNT (1.40 g, 4.7 mmol), and NMI (1.03 g, 12.6 mmol) in 6:1 DMA-DCM (35 mL) was added to Wang resin (5.00 g, subn. 0.63 mmol/g, 3.2 mmol), and the suspension was shaken at room temperature for 24 h. The resin was filtered, washed successively with DMA and DCM, and dried under high vacuum. The substitution of the resin was determined by direct cleavage of an aliquot with 20% (v/v) TFA in DCM, and subsequent analysis of the product by HPLC.

Example 3

2-(4-Carboxyphenyl)benzimidazole

Resin-bound 4-carboxybenzaldehyde (subn. 0.65 mmol/g, 400 mg, 0.26 mmol) was suspended in DMA (3 mL) and treated with 1,2-phenylenediamine (2.6 mmol) and TCNE (2.6 mmol). The suspension was sonicated for 1 h and shaken at 25° C. for an additional 22 h. The resin was filtered, washed with DMA, DCM, and dried under high vacuum. The benzimidazole was cleaved from the solid support with 20% (v/v) TFA in DCM (2×5 mL, 15 min) and the combined filtrates were evaporated to give the title compound. $^1$H NMR (d$_6$-DMSO) δ 7.35-7.43 (m, 2H), 7.69-7.78 (m, 2H), 8.19 (d, 2H, J=8.3 Hz), 8.26-8.34 (m, 2H), 12.50-14.20 (br s, CO$_2$H). MS (API-ES$^+$) m/z 239 (M+H).

Example 4

2-(4-Carboxyphenyl) methylbenzimidazole

This compound was prepared according to the procedure described in Example 3. $^1$H NMR (d$_6$-DMSO) δ 2.64 (s, 3H, CH3), 7.15-7.37 (m, 2H), 7.50-7.62 (m, 1H), 8.12-8.25 (m, 2H), 8.30-8.43 (m, 2H), 12.30-14.10 (br s, 1H, CO$_2$H). MS (API-ES$^+$) m/z 253 (M+H).

Example 5

2-(4-Carboxyphenyl)-4-hydroxybenzimidazole

This compound was prepared according to the procedure described in Example 3. $^1$H NMR (d$_6$-DMSO) δ 6.81 (d, 1H, J=7.7 Hz), 7.10-7.30 (m, 2H), 8.17 (d, 2H, J=8.3 Hz), 8.34 (d, 2H, J=7.8 Hz), 10.2-10.9 (br s, 1H, OH), 12.40-13.80 (br s, 1H, CO$_2$H). MS (API-ES$^+$) m/z 255 (M+H)

Example 6

2-(4-Carboxyphenyl)4-nitrobenzimidazole

This compound was prepared according to the procedure described in Example 3. $^1$H NMR (d$_6$-DMSO) δ 7.47 (t, 1H, J=8.1 Hz), 8.10-8.15 (m, 3H), 8.16 (d, 1H, J=8.1 Hz), 8.48 (d, 2H, J=8.4 Hz), 12.40-14.00 (br s, 1H, CO$_2$H). MS (API-ES$^+$) mz 284 (M+H).

Example 7

2-(4-Carboxyphenyl)-5-benzimidazolylcarboxylic acid

This compound was prepared according to the procedure described in Example 3. $^1$H NMR (d$_6$-DMSO) δ 7.72 (d, 1H, J=8.4 Hz), 7.89 (dd, 1H, J=8.5, 1.6 Hz), 8.14 (d, 2H, J=8.4 Hz), 8.23 (br. s, 1H), 8.32 (d, 2H, J=8A Hz), 12.20-13.80 (br. s, 2H, C0$_2$"). MS (API-ES$^+$) m/z 283 (M+H).

Example 8

2-Phenyl-4-benzimidazolylcarboxylic acid

Resin-bound N,N'-Fmoc-3,4-diaminobenzoic acid (subn.0.23 mmol/g, 350 mg, 0.081 mmol) was treated with 20% (v/v) piperidine in DMA (3×2 mL×5 min.) to remove the Fmoc protecting groups. After the third treatment, the resin was washed with DMA and DCM, and then treated with a suspension of benzaldehyde (17.4 mg, 0.164 mmol) and TCNE (21.0 mg, 0.164 mmol) in DMA (3 mL). The mixture was sonicated for 1 h, and shaken at room temperature for an additional 23 h. The resin was filtered, washed with DMA, DCM, and dried under high vacuum. The benzimidazole was cleaved from the solid support with 20% (v/v) TEA in DCM (2×5 mL, 15 min) and the combined filtrates were evaporated to give the title compound. $^1$H NMR (CD$_3$OD) δ 7.50-7.80 (m, 3H), 7.64 (d, 2H, J=8.4 Hz), 7.97 (d, 2H, J=8.4 Hz), 8.05-8.20 (m, 2H), 8.38 (s, 1H). MS (API-ES$^-$) m/z 237 (M−H).

Example 9

2-(4-Carboxyphenyl)benzoxazole

Resin-bound 4-carboxybenzaldehyde (subn. 0.60 mmol/g, 400 mg, 0.24 mmol) was treated with a solution of 2-aminophenol (262 mg, 2.4 mmol) in DMA (3 mL). The suspension was shaken at room temperature for 24 h. Tetracyanoethylene (307 mg, 2.4 mmol) was added, and the mixture stirred at room temperature for an additional 24 h. The resin was filtered, washed with DMA and DCM, and dried under high vacuum. The benzoxazole was cleaved from the solid support with 20% (v/v) TFA in DCM (2×5 mL, 15 min) and the combined filtrates were evaporated to give the title compound. $^1$H NMR (CD$_3$OD) δ 7.36-7.45 (m, 2H), 7.62-7,67 (m, 1H), 7.72-7.77 (m, 1H), 8.17 (d, 2H, J=8.3 Hz), 8.29 (d, 2H, J=8.3 Hz). MS (API-ES$^+$) m/z 240 (M+H).

Example 10

2-(4-Carboxyphenyl)benzothiazole

A solution of 2-aminothiophenol (300 mg, 2.4 mmol) in DMA (3 mL) was added to resin-bound 4-carboxybenzaldehyde (subn. 0.60 mmol/g, 400 mg, 0.24 mmol), followed by TCNE (307 mg, 2.4 mmol). The suspension was shaken at 25° C. for 24h. The resin was filtered, washed with DMA and DCM, and dried under high vacuum. The resin-bound benzothiazole was cleaved from the solid support with 20% (v/v) TFA in DCM (2×5 mL, 15 min) and the combined filtrates were evaporated to give the title compound. $^1$H NMR (d$_6$-DMSO) δ 7.52 (t, 1H, J=7.6 Hz), 7.60 (t, 1H, J=7.0 Hz), 8.12 (d, 2H, J=8.4 Hz), 8.23 (d, 2H, J=8.4 Hz), 8.00-8.40 (m, 2H). MS (API-ES$^+$) m/z 256 (M+H).

Representative structures, yields, and purities of cleaved products obtained from the condensation of resin-bound 1,2-arylenediamines, 2-aminophenols, or 2-aminothiophenols with aldehydes or cyanogen bromide, or from the condensation of resin-bound aldehydes with 1,2-arylenediamines, 2-aminophenols, or 2-aminothiophenols, are given in Table 1.

TABLE 1

Structure, Yield, and Purity of Benzimidazoles, Benzoxazoles, and Benzothiazoles Prepared on Solid phase[a,b]

| Structure | Yield | Purity |
|---|---|---|
|  | 99 | 81 |
|  | 95 | 93 |
|  | 99 | 78 |
|  | 85 | 91 |
|  | 81 | 60 |
|  | 47 | 84 |
|  | 90 | 91 |
|  | 63 | 74 |
|  | 94 | 79 |

TABLE 1-continued

Structure, Yield, and Purity of Benzimidazoles, Benzoxazoles, and Benzothiazoles Prepared on Solid phase[a,b]

| Structure | Yield | Purity |
|---|---|---|
| (benzimidazole, 5-HO2C, N-Bn, 2-NHC(O)NH-Ph) | 77 | 81 |
| (benzimidazole, 5-HO2C, 2-(4-CO2H-phenyl)) | 88 | 74 |
| (benzoxazole, 5-HO2C, 2-NHC(O)CH2-(3,4-methylenedioxyphenyl)) | 61 | 80 |
| (benzimidazole, 5-HO2C, 2-phenyl) | 99 | 65 |
| (benzimidazole, 5-HO2C, N-Bn, 2-NHC(O)CH2-(4-methylphenyl)) | 79 | 78 |
| (benzoxazole, 2-(4-CO2H-phenyl)) | 66 | 91 |
| (benzothiazole, 5-HO2C, 2-(4-(C(O)CH2Ph)-phenyl)) | 85 | 88 |
| (benzothiazole, 2-(4-CO2H-phenyl)) | 99 | 74 |
| (benzoxazole, 5-BnHNC(O), 2-(4-CO2H-phenyl)) | 88 | 85 |

[a]Purity refers to percent of product in the cleaved material, determined by HPLC.
[b]Yield refers to percent amount of product relative to the substitution level of the resin, corrected for purity.

The above description is illustrative and not restrictive. Many variations of the invention will become apparent to those skilled in the art upon review of this disclosure. Merely by way of example a range of suitable process times, reaction temperatures, and other reaction conditions may be utilized, as well as additional reaction types for creating a diverse array of compounds. The scope of the invention should therefore be determined not merely with reference to the above description, but instead with reference to the appended claims along with a full scope of equivalents.

Synthesis of Combinatorial Libraries

A number of techniques for the creation of combinatorial libraries having desired degrees of molecular diversity exist, one of which involves the use of combinatorial techniques. Suitable combinatorial techniques include those described in U.S. Pat. Nos. 5,840,500, 5,847,150, 5,852,028, 5,856,107, 5,856,496, 5,859,027 and 5,861,532. These techniques can be performed on solid or in solution phase.

The preferred process of the present invention is a solid phase synthesis (SPS) based approach. The reaction is carried out on macroscopic particles made of material insoluble in the reaction medium. The scaffold is generally linked to the surface of the support to form the scaffold-support reagent. This link is selected so that it places the compound in the reaction medium. The chemistry of the link is selected so that it can be selectively cleaved in a subsequent step, thereby releasing the synthesized product. Suitable SPS supports can be selected form commercially available resins. The scaffold-support reagent can be prepared batch wise prior to placement in the array, if desired. Each synthetic modification of the scaffold compound is prepared in sufficient quantity to permit its screening and analysis using conventional methodology, e.g., HPLC, mass spectral analysis and the assays described in the references cited in the background section.

The array of synthesized compounds is screened using conventional methodology and scored. The compounds can be chemically characterized using conventional techniques, e.g. mass spec and HPLC, before or after the screening process. The assay and individual synthetic steps can be automated. Adjustments in the synthetic approach are possible on a real-time basis.

Typically, synthesis in a 96-well plate (an 8 by 12 array) permits eight or twelve distinct scaffold resins to be distributed across the rows or down the columns, respectfully. These resins can then be reacted sequentially with any desired series of reactants. The diversity of the molecular array can be controlled to achieve any desired degree of diversity.

Typically, synthesis in a 96-well plate (an 8 by 12 array) permits eight or twelve distinct scaffold resins to be distributed across the rows or down the columns, respectfully (see Meyers et al. 1995, *Molecular Diversity* 1:13–20). These resins can then be reacted sequentially with any desired series of reactants. The diversity of the molecular array can be controlled to achieve any desired degree of diversity.

The reactions can be monitored and products characterized at each synthetic step, if desired. Reaction conditions can also be varied. Appropriate blocking groups can be added and removed to direct a desired synthesis route. These methods are capable of constructing, tens of thousands of molecules in a relatively short time span.

Incorporation by reference

To the extent necessary to understand or complete the disclosure of the present invention, all publications, patents, and patent applications mentioned herein are expressly incorporated by reference therein to the same extent as though each were individually so incorporated.

What is claimed is:

1. A process for the solid phase organic synthesis (SPOS) of substituted heterocycles selected from the group consisting of 2-substituted benzimidazoles, 2-substituted benzoxazoles, and 2-substituted benzothiazoles comprising, contacting a resin-bound aldehyde with a 1,2-arylenediamine, 2-aminophenol, 2-aminothiophenol, or substituted derivatives thereof in the presence of an oxidant in a solvent at a temperature and for a time sufficient to form a resin-bound substituted heterocycle selected from the group consisting of 2-substituted benzimidazole, 2-substituted benzoxazole, and 2-substituted benzothiazole and optionally contacting the formed resin-bound substituted heterocycle selected from the group consisting of 2-substituted benzimidazole, 2-substituted benzoxazole, or 2-substituted heterocycle selected from the group consisting of 2-substituted benzimidazole, 2-substituted benzoxazole, or 2-substituted benzothiazole from the resin, wherein 1) either the aldehyde or the precursor is covalently bound to a resin, forming the solid phase, 2) the oxidant is selected from the group consisting of p-chloranil (CA), 7,7,8,8-tetracyanoquinodimethane (TCNQ), benzylidene-malononitrile (BMCN), tetracyanoethylene (TCNE), 2,3-dicyano-1,4-benzoquinone (DCBQ), or 2,3-dichloro-5,6-dicyano-1,4-benzoquinone (DDQ) and 3) the mild conditions include a reaction temperature of room temperature or a temperature of about 40–60° C. and a reaction time of 48 hours or less.

2. The method of claim 1 wherein the reaction temperature is room temperature.

3. The method of claim 1 wherein the reaction temperature is about 40–60° C.

4. The method of claim 1 wherein the solvent is selected from the group consisting of methanol (MeOH), ethanol (EtOH), acetonitrile (MeCN), dimethylformamide (DMF), dimethylacetamide (DMA) and mixtures thereof.

5.

6. The method of claim 1 wherein the reaction temperature is room temperature, the solvent is dimethylacetamide (DMA), and the oxidant is tetracyanoethylene (TCNE).

7. The method of claim 1, wherein the acid is trifluoroacetic acid (TFA) in dichloromethane (DCM).

8. The method of claim 1 wherein the resin-bound aldehyde is 4-carboxybenzaldehyde.

9. The method of claim 1 wherein the resin-bound precursor is N,N'-Fmoc-3,4-diaminobenzoic acid.

10. The method of claim 1 wherein the benzimidazole is selected from the group consisting of 2-(4-Carboxyphenyl) benzimidazole; 2-(4-Carboxyphenyl)-4-methyl-benzimidazole; 2-(4-Carboxyphenyl)-4-hydroxybenzimidazole; 2-(4-Carboxyphenyl)-4-nitrobenzimidazole; 2-(4-Carboxyphenyl)-5-methylbenzimidazole; 2-(4-Carboxyphenyl)-5- benzimidazolylcarboxylic acid; 2-Phenyl-4-benzimidazolylcarboxylic acid; and 2-(4-Carboxyphenyl)benzoxazole; 2-(4-Carboxyphenyl)benzothiazole.

11. The method of claim 1 wherein the precursor is present relative to the aldehyde and the oxidant in a ratio from about 1:1.1:1.1 to about 1:100:100.

12. The method of claim 1, wherein the ratio is from about 1:1.1 to about 1:25.

13. The method of claim 1, wherein the ratio is from about 1:1.1:1.1 to about 1:25:25.

14. The method of claim 13, wherein the ratio is from about 1:1.1:1.1 to about 1:10:10.

15. The method of claim 7, wherein the acid is trifluoroacetic acid (TFA) in dichloromethane (DCM).

* * * * *